United States Patent [19]
Patel et al.

[11] Patent Number: 6,165,454
[45] Date of Patent: *Dec. 26, 2000

[54] STABILIZED HAIR CARE PRODUCTS

[75] Inventors: Amrit Patel, Dayton; Tracey Aldrich, Somerset; Bret Schweid, Avenel, all of N.J.

[73] Assignee: Colgate-Palmolive Company, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/933,521

[22] Filed: Sep. 18, 1997

[51] Int. Cl.⁷ .............................. A61K 7/06; A61K 7/11; A61K 7/08; A61K 7/075
[52] U.S. Cl. .................. 424/70.11; 424/70.12; 424/70.17; 424/70.15; 424/70.19
[58] Field of Search .............. 424/70.11, 70.12, 424/70.17, 70.15, 70.19

[56] References Cited

U.S. PATENT DOCUMENTS

| | | |
|---|---|---|
| Re. 34,584 | 4/1994 | Grote et al. . |
| 4,203,859 | 5/1980 | Kirn et al. . |
| 4,673,571 | 6/1987 | Mahieu et al. . |
| 4,704,272 | 11/1987 | Oh et al. . |
| 4,741,855 | 5/1988 | Grote et al. . |
| 4,854,333 | 8/1989 | Inman et al. . |
| 5,037,648 | 8/1991 | Joiner . |
| 5,073,296 | 12/1991 | Kopolow et al. . |
| 5,084,208 | 1/1992 | Negrin . |
| 5,151,210 | 9/1992 | Steuri et al. . |
| 5,152,914 | 10/1992 | Forster . |
| 5,169,622 | 12/1992 | Kopolow . |
| 5,169,623 | 12/1992 | Kopolow . |
| 5,234,682 | 8/1993 | Machio et al. . |
| 5,252,324 | 10/1993 | Bires et al. . |
| 5,344,643 | 9/1994 | Thiel et al. . |
| 5,362,415 | 11/1994 | Egraz et al. . |
| 5,393,452 | 2/1995 | Raleigh et al. . |
| 5,417,965 | 5/1995 | Janchitraponvej ............ 424/70.12 |
| 5,474,712 | 12/1995 | Dotolo et al. . |
| 5,536,332 | 7/1996 | Chun . |
| 5,543,074 | 8/1996 | Hague et al. . |
| 5,585,104 | 12/1996 | Ha et al. . |
| 5,637,306 | 6/1997 | Cauwet et al. . |
| 5,648,323 | 7/1997 | Coffindaffer et al. . |
| 5,650,383 | 7/1997 | Dubief et al. . |
| 5,656,257 | 8/1997 | Fealey et al. . |
| 5,756,436 | 5/1998 | Royce et al. . |
| 5,837,661 | 11/1998 | Evans et al. . |

FOREIGN PATENT DOCUMENTS

| | | |
|---|---|---|
| 000463780A2 | 1/1992 | European Pat. Off. . |
| 0463780 | 1/1992 | European Pat. Off. . |
| 0466184 | 1/1992 | European Pat. Off. . |
| 0550 656B1 | 7/1993 | European Pat. Off. . |
| WO9509599 | 10/1993 | European Pat. Off. . |
| 0615 742A1 | 9/1994 | European Pat. Off. . |
| 1166062 | 10/1969 | United Kingdom . |
| WO 99/13837 | 9/1997 | WIPO . |

*Primary Examiner*—Carlos A. Azpuru
*Attorney, Agent, or Firm*—Rosemary M. Miano

[57] ABSTRACT

A low energy method for making stabilized hair care products comprising an anionic detersive surfactant, a water-insoluble silicone and acrylic stabilizing agent is disclosed wherein the method does not require added heat.

32 Claims, No Drawings

STABILIZED HAIR CARE PRODUCTS

FIELD OF THE INVENTION

This invention relates to an improved method of stabilizing hair care products comprising water insoluble organosilicone compounds such as dimethicone by using an energy saving process which does not require high temperatures.

BACKGROUND OF THE INVENTION

One of the most prominent ingredients in a conditioning hair care products such as a conditioning shampoo (also called a "2 in 1" shampoo product) is a silicone and/or its derivatives. While it is desirable to add high molecular weight silicone derivatives to shampoos to achieve conditioning effects, it can be difficult to formulate surfactant insoluble silicone-containing shampoos that are stable and do not have the problem of separating out the silicone component. Various attempts at incorporating these silicone conditioning agents into such conditioning shampoos have included dispersing, suspending or emulsifying such agents; these approaches result in the opacification of the products and sometimes results in unstable products due to the separating out of the silicone. Higher levels of a silicone material such as dimethicone are useful in providing increased amounts of conditioning to the hair. However, higher levels of dimethicones are very difficult to physically stabilize in detergent systems.

There have been various attempts at solving the separation problem. For example, one method of stabilizing dimethicones uses alcohols having 20–40 carbons, such as are commercially available. Such compositions are found in U.S. Pat. No. 5,213,716 to Patel et al, U.S. Pat. No. 4,997,641 to Hartnett et al, and assigned to the same assignee as this application. Another method is found in U.S. Pat. No. 4,741,855 to Grote et al, which teaches the use of long chain ($C_{16}$–$C_{22}$) acyl derivatives such as ethylene glycol distearate or long chain ($C_{16}$–$C_{22}$) amine oxides, as suspending agents. U.S. Pat. No. 5,152,914 to Forster et al teaches the use of suspending agents chosen from polyethylene glycol mono- or diesters of ($C_{16}$–$C_{22}$) fatty acids having from 2–7 ethylene oxide groups. U.S. Pat. No. 4,704,272 to Oh et al. Teaches the use of xanthan gum and long chain acyl derivatives as suspending agents for insoluble, non-volatile silicone.

There have also been approaches to silicone chemistry in personal care and shampoo products which have used different chemistries in order to obtain better products.

U.S. Pat. No. 5,543,074 to Hague et al describes personal washing compositions comprising silicone oil and a suspending agent selected from polyacrylic acid, copolymers of acrylic acid with hydrophobic monomers, and copolymers of acrylic acid and acrylate esters.

U.S. Pat. No. 5,073,296 to Kopolow et al teaches a method of stabilizing an oil-in-water emulsion using a water-soluble vinyl compound and a free-radical polymerization initiator. The oil may be a cosmetically active material such as silicone oil. A comonomer such as a methacrylate or a neutralized acrylic acid may be added to the vinyl compound.

Further references for hair care compositions with insoluble silicones include U.S. Pat. No. 4,997,641 to Hartnett et al and U.S. Pat. No. 5,415,857 to Robbins et al, both assigned to the same assignee as this application.

Other references which relate to personal care and which may comprise silicone oils which are stabilized by the addition of vinyl monomers and acryl comonomers which are polymerized in-situ include U.S. Pat. No. 5,084,208 to Negrin et at; U.S. Pat. No. 5,169,622 to Kopolow et al; U.S. Pat. No. 5,169,623 to Kopolow et al; U.S. Pat. No. 5,474,712 to Dotolo et al (conditioning shampoo which consists of, inter alia, a polyalkyleneoxide-modified polydimethyl siloxane and polyacrylic acid and acrylic copolymer emulsifier); U.S. Pat. No. 5,037,648 to Joiner (skin conditioning preparation with, inter alia, polyacrylic acid and dimethicone); and U.S. Pat. No. 5,234,682 to Machio et al (includes a cosmetic composition consisting essentially of, inter alia, dimethicone and acrylates copolymer).

Other hair care references include U.S. Pat. No. 5,051,250 to Patel et al and U.S. Pat. No. 5,346,642 to Patel et al, both assigned to the same assignee as this application.

Some of these methods require the use of heat to get the silicone and the $C_{20}$–$C_{40}$ into solution and thus increase the batch time.

There still remains a need to have a 2-in-1 shampoo composition which successfully incorporates a water insoluble non-volatile silicone into a composition which has good stability.

It is a further object to obtain a hair care composition which successfully incorporates a water insoluble silicone into a composition for hair which and which can be manufactured by a low energy process.

Thus, it is an object of this invention to provide an improved method of stabilizing a water insoluble silicone material such as dimethicone and a composition made by such method which is suitable for hair care use. It is a further object of this invention to provide a method for stabilizing a silicone material such as dimethicone which does not require high temperatures. It is yet another object of the invention to provide a method for stabilizing a silicone material such as dimethicone which reduces batch time. These and other objects of the invention will be apparent from the following description.

SUMMARY OF THE INVENTION

This invention comprises a method of stabilizing water insoluble organosilicone compounds such as dimethicones and silicones (especially aminosilicones (also called amodimethicone)) which are suitable for use in hair care products (such as conditioning shampoos or hair conditioners) to form a solution containing a mild, aqueous, foaming and conditioning, detergent composition comprising by weight based on the total weight of the composition:
A. 4.00–50.00 percent of a detersive surfactant selected from the group consisting of an anionic detergent selected from the group consisting of $C_8$–$C_{18}$ alkyl sulfates, $C_8$–$C_{18}$ alkyl ethenoxy ether sulfates containing 1–5 ethenoxy groups in the molecule, $C_{10}$–$C_{18}$ acyl isethionates, $C_{10}$–$C_{20}$ alkyl sulfonates, $C_{10}$–$C_{20}$ alkylene sulfonates, and mixtures thereof; and optionally at least one of:
(1) 0.10–5.00 percent of an anionic hydrotropic, $C_1$–$C_3$ alkyl benzene sulfonate or $C_5$–$C_6$ alkyl sulfate;
(2) 0.10–15.00 percent of an amphoteric surfactant selected from the group consisting of $C_8$–$C_{18}$ alkyl betaines, $C_8$–$C_{18}$ alkyl sulfobetaines, $C_8$–$C_{18}$ alkylamido $C_2$–$C_3$ alkyl betaines, $C_8$–$C_{18}$ alkylamido $C_2$–$C_3$ alkyl sulfobetaines, $C_8$–$C_{18}$ alkyl amphoacetates, $C_8$–$C_{18}$ alkyl amphopropionates, and mixtures thereof; and
(3) 0.1–4.0 percent of a nonionic surfactant, particularly a member of the group consisting of $C_8$–$C_{22}$ monoethanolamides and mixtures there of and $C_8$–$C_{22}$ diethanolamides and mixtures thereof, especially cocomonoethanolamide and cocodiethanolamide, and more especially cocodiethanolamide;
provided that the total amount of detersive surfactant does not exceed 50 percent by weight of the total weight of the composition and, preferably, is in the range of 6–30 percent;

B. 0.01–10.00 percent of a water-insoluble conditioning agent which is selected from the group consisting of:
  (1) 0.10–6.00 percent of a water-insoluble silicone selected from the group consisting of dimethicones and silicones as described below in more detail; and
  (2) a mixture of at least one of B(1) with 0.01–3.00 percent of a cationic polymer such as a polyquaternary compound selected from the group consisting of quaternized cellulosic polymers (in particular at least one quaternized cellulosic polymer) and a mixture of at least one quaternized cellulosic polymer with a non-cellulosic quaternary conditioning polymer;
C. 0.10–5.00 percent of an acrylic stabilizing agent selected from the group consisting of polyacrylic acid, derivatives of polyacrylic acid, acrylates copolymer and derivatives of acrylates copolymer;
D. the balance as water or aqueous medium.

DETAILED DESCRIPTION OF THE INVENTION

While general ranges of each of the components have been listed above, more particular ranges and selections are as follows.

Particular water insoluble organosilicone compounds include:
  (a) dimethicones, dimethicone derivatives and mixtures of the foregoing having a viscosity in the range of 5–100,000 centipoise (cps), particularly 30–70,000 and even more particularly 60,000; for example organosilicone compounds of Formula I:

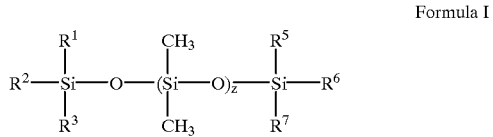

Formula I wherein $R^1$, $R^2$, $R^3$, $R^5$, $R^6$, and $R^7$ are alkyls of 1–6 carbons (especially 1–2 carbons) and z is selected so that the viscosity described above is achieved; and
  (b) aminosilicones of Formula II

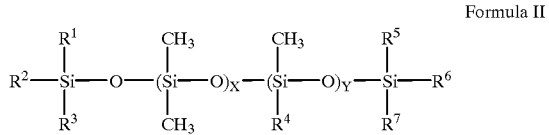

Formula II wherein $R^1$, $R^2$, $R^3$, $R^5$, $R^6$, and $R^7$ are alkyls of 1–6 carbons (especially 1–2 carbons); and $R^4$ is $R^8$—NH—$CH_2CH_2$—$NH_2$, $R^8$ is an alkylene of 3–6 carbons;
x= is an average value and is a number in the range of 500–10,000, particularly 500–4,000, more particularly 500–1000, and especially 750–800; and
y= is an average value and is a number in the range of 1–10, particularly less than 5 and especially 1.

The dimethicones and silicones previously described can be used in mixtures, especially mixtures where high viscosity materials are mixed with lower viscosity materials. Examples of suitable materials include a dimethicone from Dow Corning (Midland, Mich.) known as Dow Corning Fluid 200 and a dimethicone from Union Carbide (Tarrytown, N.Y.) known as Silicone L-45.

Acrylic stabilizers may be selected from the group consisting of acrylic acid derivatives and their copolymers. Examples of such compounds may be represented by Formula III and Formula IV:

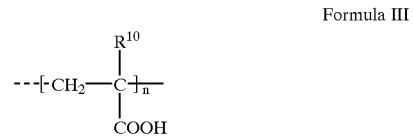

Formula III where $R^{10}$ is a member of the group consisting of hydrogen and $C_1$–$C_{22}$ alkyl group;
and n is an average value and is a number from 3–9200, preferably 3–4100, and is selected so that the molecular weight is in the range of 218–2,000,000, particularly 218–1,500,000, especially 218–1,000,000; and

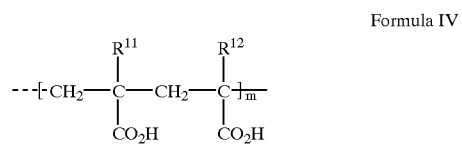

Formula IV where $R^{11}$ and $R^{12}$ are each independently selected from the same group defined for $R^{10}$, and m is selected from the same group as defined for n.

For the acrylic acid derivatives and their copolymers compounds any of the acid groups may be:
  (a) neutralized by a member selected from the group consisting of cosmetically acceptable bases such as sodium hydroxide; phosphates such as sodium phosphate, dibasic; any other basic salt suitable for use in cosmetic products; and amines such as $C_3$–$C_{22}$ aliphatic amines (especially primary alkyl amines).
  (b) esterified with a member of the group consisting of $C_3$–$C_{22}$ aliphatic alcohols.

Additionally the acrylic acid derivatives and their copolymers can be used to form a complex with a cationic compound such as cetyl trimethyl ammonium chloride or distearyl diammonium chloride, and polycationics made with such cationic complexes.

Examples of suitable stabilizing agents include acrylates/steareth-20 methacrylate copolymer (for example, ACULYN® 22, from Rohm & Haas, Philadelphia, Pa.) and acrylates copolymer (for example, ACULYN® 33; ACUSOL®-445, –810, and –830; and ACRYSOL® ASE 75 from Rohm & Haas). For the ACULYN-33 product (having a pH of approximately 3.8), a neutralization step is performed with sodium phosphate (such as disodium phosphate), sodium hydroxide or a cosmetically acceptable organic amine to increase the pH to approximately 6.5. The stabilizing agents should be of a grade and purity acceptable for cosmetic use or purified as needed to be cosmetically acceptable.

More particular values for the groups described above are as follows.

For the detersive surfactant mixture more particular groups and ranges are:
  (1) 1.00–35.0 percent, especially 5.00–30.0 percent, and, more particularly, 6.00–30.0 percent of an anionic detergent selected, for example, from the group consisting of water soluble lipophilic sulfates and/or sulfonates of 8–22 carbon atoms, preferably of 10–20 carbon atoms, more preferably 10–16 or 10–18 carbon atoms, and most preferably 12–16 or 12–18 carbon atoms. Among such anionic detergents there may be mentioned, as examples thereof, higher (10–18 carbons) alkyl sulfates, higher (10–18 carbons) paraffin sulfonates, higher (10–18 carbons) olefin sulfonates, higher (10–18 carbons) fatty acid monoglyceride sulfates, higher (10–18 carbons) fatty alcohol lower (C1–C6) alkoxy (and polyoxy) sulfates, linear higher (10–18 carbons) alkyl benzene sulfonates and dialkyl sulfosuccinates. The most preferred of these anionic detergents is the higher (10–18 carbons) alkyl sulfates of 10–16 carbon atoms and the higher alkyl lower alkoxy sulfates of 10–18 carbon atoms (preferably with the higher alkyl thereof being lauryl and with 2 or 3 ethoxy groups per mole). However, such alkyls may be of 12–16 carbon atoms and the alkoxy content may be of 1–20 per mole, such as 2–6 ethoxy groups per mole. A most preferred higher fatty alcohol sulfate is lauryl sulfate, and a particularly preferred higher fatty alcohol poly-lower alkoxy sulfate is di- or triethoxylated lauryl alcohol sulfate. Most preferably the anionic detergent will be a mixture of higher (10–18 carbons) alkyl sulfate and higher (10–18 carbons) alkyl ether sulfate, with either being present in greater or equal proportion, and with the ratio of amounts of such components being in the range of 10:1 to 1:10, especially 7:1 to 1:7, for example, 1:5 to 5:1, when both such anionic detergents are present. The anionic detergents will usually be employed in the forms of their water soluble salts, which will usually be salts of alkali metals (sodium, potassium), ammonium, amines (such as dimethylamines and trimethylamine) or lower alkanolamines (such as triethanolamine, diethanolamine and monoethanolamine). Particular examples of suitable anionic detergents include sodium lauryl sulfate with 2 moles of ethoxylation ("SLES") and corresponding ammonium salt and the triethanolamine salt thereof; olefin sulfonate; tridecyl benzene sulfonate; $C_{12}$–$C_{16}$ acyl monoglyceride sulfate;

(2) 0.05–10.00 percent and, more particularly, 0.05–5.00 percent of an anionic hydrotrope, for example, sodium cumene sulfonate, sodium benzene sulfonate; and (3) 0.50–15.00 percent and, more particularly, 1.00–10.00 percent of an amphoteric surfactant selected from, for example, cocoamidopropylbetaines, sodium laureth-2-sulfosuccinate, amphopropionic acid, cocamidobetaine, cocobetaine, cocobetainamido sodium lauriminodipropionate, dodecyl dimethylamine oxide, octyl dimethylamine oxide, octadecyl dimethylamine oxide, cocamidopropylamine, cocoamphodipropionic acid, cocamidopropylhydroxy sultaine.

Another particular groups is an anionic detergent is selected from the group consisting of $C_{12}$ alkyl $C_{2-3}$ alkoxy sulfate, $C_{12}$ alkyl ethoxy sulfate and $C_{10}$–$C_{18}$ fatty alcohol ethoxy sulfates.

The cationic polymers suitable for use with this invention include derivatives of natural polymers such as cellulose and gums. These derivatives are water-soluble to the extent of at least 0.5 percent by weight at 20 degrees C. Generally such polymers have more than 10 monomer units in their molecules and a molecular weight of about 1000–1,00,000, preferably 2000–500,000. Usually the lower the molecular weight the higher the degree of substitution by the cationic, usually quaternary, group.

Particular materials are those where the cationic portion is a quaternary group such as, for example, where the quaternary group is an alkyl ammonium group selected from the group consisting of $C_8$–$C_{22}$ amidopropyl dimethylamine lactate, $C_8$–$C_{22}$ amidopropyl morpholine lactate; $C_8$–$C_{22}$ amine oxide; dimethylamine lactate; and mixtures thereof.

Suitable natural polymers which may be converted into the desired cationic polymers are hydroxy alkyl celluloses and alkyl hydroxy alkyl celluloses. Cationic hydroxy alkyl celluloses and their preparation are described in British Patent Number 1,166,062 assigned to Union Carbide. These hydroxy ethyl celluloses are marketed under the trade designation JR 125, JR 30M and JR 400 and are believed to have a molecular weight of 150,000–400,000 and a degree of substitution off a quaternary group of about 0.3. Polyquaternium-10 is a polymeric quaternary ammonium salt of hydroxyethyl cellulose reacted with a trimethyl ammonium substituted epoxide and is the name for this previous class of materials. Other polyquaternium materials may also be useful. These include products known as Polyquaterniums with numbers 1, 2, 4, 5, 7–9, 11–20, 22, 24, 27–30, especially Polyquaternium-6, Polyquaternium-7; Polyquaternium-10. Alkyl hydroxy alkyl celluloses having the same formula as hydroxy alkyl cellulose, but with additional alkyl substituents at other sites on the anhyhdroglucose unit also are available. More particularly, the ethyl hydroxy ethyl celluloses are available under the trade name "MODOCOLL" with a molecular weight in the range of about 50,000–500,000 and a degree of substitution of about 0.1–0.8.

Other suitable natural cationic polymers are the galactomannan gums, for example, guar gum and hydroxy alkylated guar gum, especially cationic guar gum. The molecular weight of guar gum is believed to be from about 100,000–1,000,000. A suitable cationic guar gum carrying the group —$CH_2CH=CHCH_2N(CH_3)_3Cl^{-1}$ with a degree of substitution of about 0.2–0.8 is commercially available under the trade names JAGUAR C-17 and C-13.

The proportion of the cationic natural polymer usually will be from about 0.05 percent to 1.0 percent, more particularly from 0.1 percent to 0.8 percent and, more particularly, from 0.1 percent to 0.5 percent by weight of the final composition.

When the cationic natural cellulose or galactomannan gum polymers are present in the inventive compositions, up to one half of the natural polymer may be substituted by a second non-cellulosic, cationic polymer, having conditioning properties, provided that the non-cellulosic cationic polymer is soluble in the final composition. Examples of such cationic polymers are dialkyldiallyl ammonium salt (for example, a halide) homopolymers and copolymers, for example, dimethyldiallyl ammonium chloride homopolymer, dimethyldiallyl ammonium chloride/acrylamide copolymer containing at least 60 percent dimethyldiallyl ammonium chloride monomer, dimethyldiallyl ammonium chloride/acrylic acid copolymer containing at least 90 percent dimethyldiallyl ammonium chloride monomer, vinyl imidazole/vinyl pyrrolidone copolymers containing at lest 50 percent vinyl imidazole and polyethyleneimine. Particular cationic polymers include MERQUAT 100 (a polymer of diallyldimethyl ammonium chloride (charge density of 126)) and LUVIQUAT 905 (a 95 percent vinyl imidazole/5 percent vinylpyrrolidone copolymer (charge density of 116)). Other non-cellulosic cationic polymers are disclosed in the *CTFA Cosmetic Ingredient Dictionary* (6th edition, 1995) under the designation "Polyquaternium" followed by a whole number, which reference list is incorporated by reference herein.

In addition to the required components of the conditioning compositions of the invention, including the conditioning shampoos which are described herein, there may also be present in such compositions various adjuvants which are known in the art to impart desirable properties or which are believed to be useful when incorporated into the compositions of the present invention. Optionally other ingredient may be added to formulate the shampoo compositions. These include:

(a) other conditioning agents selected from the group consisting of paraffins, petrolatums, microcrystalline waxes, isoparaffins, mineral oils and polyethylenes (accompanied by a solubilizing hydrocarbon). All of which have been described in application Ser. No. 07/369,361, now abandoned, and in our. U.S. Pat. Nos. 5,051,250 and 5,415,857;

(b) higher (10–18 carbons) fatty acid esters of lower (C1–C6) alcohols, lower (C1–C6) fatty acid esters of higher (10–18 carbons) alcohols, and higher (10–18 carbons) fatty acid esters of higher (10–18 carbons) fatty alcohols and mixtures as described in our U.S. Pat. No. 5,415,857;

c) thickeners such as water soluble polymers, for example, lower alkyl celluloses, and hydroxy-lower alkyl celluloses (for example, methyl cellulose and hydroxypropyl methyl cellulose), and gums such as xanthan gum and guar gum, which may also act as stabilizers for the aqueous compositions, sodium chloride (in an amount not greater than 1 percent by weight);

d) foam modifiers and improvers (also called foam booster.) such as higher fatty acid triglycerides, and higher fatty acid alkanolamides (for example, betaines, coco-amidopropyl betaine), $C_{18}$–$C_{36}$ acids triglycerides and lauric monoethanolamide;

e) pearlescing agents such as ethylene glycol mono- and distearates such as in an amount of 0.1–3.0 percent by weight;

f) therapeutic agents such as salicylic acid, selenium sulfide, and anti-dandruff agents such as zinc pyrithione and climbazole such as in an amount of 0.1–3.0 percent by weight;

g) viscosity controlling agents such as propylene glycol and sodium chloride such as in an amount of 0.1–3.0 percent by weight;

h) fragrance such as in an amount of 0.05–1.5 percent by weight;

i) antibacterials and preservatives such as GERMABEN II, GERMABEN II-E, GERMALL 115, GERMALL II (from Sutton Laboratories, Inc., Chatham, N.J.), KATHON CG AND KATHON CG II (from Rohm & Haas, Philadelphia, Pa.), such as in an amount of 0.01–0.02 percent by weight;

j) coloring agents such as dyes and dispersible pigments, for example, all D&C and FD&C colors approved for use in cosmetic products such as in an amount of 0.0001–0.1 by weight;

k) sequestrants such as ethylene diamine tetraacetic acid (or a suitable derivative thereof such as the acetate or sodium salt) ("EDTA") such as in an amount of 0.01–0.30 percent by weight;

l) pH adjusters;

The invention also comprises a method for making such stabilized compositions. The major advantage of this process is that it does not require the use of elevated temperature in order to make the stabilized compositions. The method comprises combing the ingredients using conventional mixing equipment using the following steps:

A) form a main mixture by combining water and surfactant;

B) separately prepare a dispersion of a cationic polymer such as a polyquaternium compound in water;

C) add the dispersion of cationic polymer in water to the main mixture of water and surfactant to form a gel and continue mixing, preferably until the gel is clear, smooth and homogeneous;

D) adjust the pH of the mixture to 5.0–8.0 such as by the addition of sodium phosphate dibasic;

E) add a surfactant to the mixture such as sodium cumene sulfonate ("SCS") and mix until uniform;

F) separately add a first portion of the fragrance, if desired, in combination with a thickening agent such as cationic guar gum to the mixture;

G) disperse a thickening agent (optionally with the first portion of fragrance), then add the dispersion to the main mixture, and mix until uniform;

H) separately prepare a mixture of a foam booster and thickening agent such as cocodiethanolamide ("CDEA") with disteryldiammonium chloride ("DSDAC") and, optionally, any remaining portion of the fragrance, and mix until preferably the solution of these materials is clear (if desired, a low level of heat or the upper range of ambient temperature may be used, such as in the range of 30–35 degrees);

I) combine the mixture of part "H" with the main mixture until uniform;

J) add the stabilizing component, for example, acrylates copolymer, to the main mixture and mix until uniform;

K) add the dimethicone to the main mixture and mix until uniform;

L) add in other optional ingredients either alone or in combination to the main mixture and continue mixing until the mixture is uniform;

M) cool the mixture to 25 degrees if needed;

N) adjust pH of the mixture as necessary;

O) adjust viscosity of the mixture as necessary; and

P) filter product.

In the final products made by this method, the viscosity will be in the range of 1500–10,000 cps, and particularly 4500±cps; the pH will be in the range of 4–8, particularly 5–7 and more particularly 6–7; and the specific gravity will be in the range of 0.99–1.01, particularly 0.995±0.01.

In evaluating the stability of the shampoos made according to this invention, storage tests can be done. Storage for a selected period of time at a temperature of 49 degrees C may be undertaken to see if any separation of product contents occurred. If separation does not occur after three months, the product is judged as stable with acceptable viscosity, pH, emulsion stability, and color.

EXAMPLES

The following non-limiting examples are described as illustrating and explaining the invention. Chemical symbols, terms and abbreviations have their usual and customary meanings. Unless otherwise indicated, all percents and all numbers listed in the tables and elsewhere in this description are in weight percents based on the total weight of the composition as 100 percent. The term "Sep'd" means the composition separated. The term "cps" means centipoise. The term "cst" means centistokes. The term "OK" means that the composition exhibited acceptable stability characteristics. Other abbreviation used have been defined elsewhere in this application.

Basic Method

A main mixing vessel is selected and equipped with a variable speed "Lightnin' Mixer". The main mixing vessel should be stainless steel (304L or 316L or their equivalent). The other mixing vessels (for example used in Parts 2 and 4) may be stainless steel or plastic and selected to be suitable for the materials used, except that a separate stainless steel vessel as described for the main mixing vessel is needed for Part 5. The vessel for Part 5 should be equipped for minimal mixing and, optionally, heating. Vacuum equipment is not required, but care must be taken not to promote foam formation. Additional equipment may be used if desired.

1. To the main mixing vessel add suitable amounts of water (preferably deionized water) and surfactant (for example, ammonium lauryl sulfate ("ALS")). Mix until uniform.

2. To a separate, dry, clean container, add a suitable amount of unheated, room temperature water (preferably deionized water). Disperse a suitable amount of a cationic polymer (for example, Polyquaternium-10) in the water. Mix well until this premix is free of lumps, but do not mix longer than 5 minutes just prior to addition or it may gel. Add this premix of Part 2 to the main mixing vessel. Mix the contents of the main vessel for at least 15 minutes or until the gel is clear, smooth and shiny. This should be accomplished before continuing.

3. Add a suitable amount of sodium phosphate dibasic to control pH and a suitable amount of sodium cumene sulfonate ("SCS") to control viscosity to the main mixing vessel. Mix the batch for at least 15 minutes or until uniform.

4. To a separate, dry, clean container add a suitable amount of fragrance. Sprinkle in a suitable amount of cationic guar gum into the fragrance with mixing. Continue mixing until the cationic guar gum is completely dispersed and free of lumps. Add this mixture from Part 4 to the main mixing vessel and mix the contents of the main mixing vessel for at least 15 minutes or until uniform.

5. To a separate, heatable, dry clean container add a suitable amount of each of cocodiethanolamide ("CDEA") and distearyl diammonium chloride ("DSDAC") and about half of the allocated amount of fragrance. Mix until the solution is clear. Optionally low heat may be applied to raise the temperature to 30–35 degrees C. This material is then added to the main mixing vessel and the contents stirred for at least 15 minutes or until uniform.

6. A suitable amount of acrylates copolymer (or other acrylic stabilizing agent) is then added to the main mixing vessel. The contents are mixed for at least 15 minutes or until uniform. A suitable amount of Dimethicone (60,000 cst) is added to the main mixing vessel and the contents are mixed for at least 15 minutes or until uniform.

7. To a separate, dry, clean container is added suitable amounts of water (preferably deionized water) Goldschmidt TegoPearl N-100 and colors. This mixture is mixed for at least 15 minutes or until uniform. The remaining material from Part 7 is then added to the main mixing vessel with mixing. The mixing is continued for at least 15 minutes or until uniform.

8. A preservative such as KATHON CG is added to the main mixing vessel and mixing is continued for at least 15 minutes or until uniform.

9. If needed the product is cooled to 25 degrees C. Specifications are checked on the batch sample. If necessary, sodium phosphate dibasic is added to increase pH, sodium phosphate monobasic is added to decrease pH; sodium cumene sulfonate (SCS) is added to reduce viscosity, CDEA is added to increase viscosity. If sodium chloride is used as a thickener, the amount should not exceed 1 percent by weight based on the total weight of the composition.

Base Examples 1–3

Formulations for Stability Evaluation

The following Base Examples were made using the Basic Method described above with the amounts of materials described in the Table A. Various stabilizing agents were added in later examples.

TABLE A

| Ingredient | Base Example 1 | Base Example 2 | Base Example 3 |
|---|---|---|---|
| Filtered, irradiated, deionized water | q.s. | q.s. | q.s. |
| Ammonium lauryl sulfate ("ALS") (28%) | 50.00 | — | 50.00 |
| Sodium laureth sulfate-2 ethylene oxide ("SLES 2EO") (28%) | — | 42.85 | — |
| Cocoamidopropyl Betaine ("CAP Betaine") (30%) | — | 13.34 | — |
| Cocodiethanol amine ("CDEA") (90%) | 2.00 | — | 2.00 |
| Polyquaternium-10 (100%) | 0.15 | 0.15 | 0.15 |
| Sodium phosphate monobasic | ±0.30 | ±0.30 | ±0.30 |
| Sodium phosphate dibasic | — | — | — |
| Cationic guar gum | 0.20 | 0.20 | 0.20 |
| Stabilizer with C20–C40 alcohols (UNILIN ® 425) | — | — | 2.00 |
| Distearyl diammonium chloride ("DSDAC") | 0.20 | 0.20 | 0.20 |
| Dimethicone - 60,000 centistokes | 3.00 | 3.00 | 3.00 |
| Sodium cumene sulfonate | ±0.50 | ±0.50 | ±0.50 |
| Miscellaneous (preservative, perfume, color) | q.s. | q.s. | q.s. |
| TOTAL | 100.00 | 100.00 | 100.00 |

Base Examples 1 and 2 were used to investigate the stability of dimethicone 60,000 cst by using different types of stabilizers. The materials listed in Table B (or similar materials obtained from another supplier) stabilized compositions made according to Base Examples 1 and 2 at a level of 2% active (or 7.14% in the commercially available form) (based on the weight of the total composition as 100 percent). Note that the ACULYN-33 product was neutralized with disodium phosphate. Only one base was used at a time.

TABLE B

| Material | Use level (% active) |
|---|---|
| Acrylates/steareth-20 methacrylate copolymers (ACULYN ® 22, 28%) | 2.00 |
| Acrylates/steareth-20 methacrylate copolymers (ACULYN ® 33, 30%) | 2.00 |
| Acrylates/steareth-20 methacrylate copolymers (ACUSOL ® 830, 30%) | 2.00 |
| Distearyl-phthalic acid amide ("SAB-2") | 2.00 |
| Di(hydrogenated)tallow-phthalic acid amide ("TAB-2") | 3.00 |
| Polyacrylic acid (ACRYSOL ® ASE 75) | 2.00 |
| Polyacrylic acid (CARBOPOL ® 907) | 2.00 |

The base formulation of Example 3 was used as the control, in which a material having C20–C40 alcohols in a mixture with an average molecular weight of 425 (UNILIN® 425) was used as the silicone stabilizer. (Usually at least 1.5–2.0 percent of this material is used to stabilize 1–4 percent of silicone in a shampoo composition.) The formulation of Example 3 was evaluated for stability and was stable when evaluated after one month at 49 degrees C without any separation of the dimethicone. After 1 month, a slight separation can be noticed at the bottom of the sample in a clear glass jar. This is considered normal for a shampoo which contains this type of silicone.

Examples 1–10

Dimethicone Stabilization

The following Examples were made by the Basic Method described above. using the amounts of materials shown in Table C.

TABLE C

| Ingredient | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Water | q.s. | q.s. | q.s. | q.s. | q.s. | q.s. | q.s. | q.s. | q.s. | q.s. |
| ALS (28%) | 46.50 | 46.50 | 46.50 | 46.50 | 46.50 | 46.50 | 46.50 | 46.50 | 46.50 | 46.50 |
| CDEA | 2.00 | 2.00 | 2.00 | 2.00 | 2.00 | 2.00 | 2.00 | 2.00 | 2.00 | 2.00 |
| ACULYN ® 33 (28%) | — | 8.90 | 7.14 | 6.25 | 5.90 | 5.35 | 4.46 | 3.57 | — | — |
| ACULYN ® 22 (30%) | — | — | — | — | — | — | — | — | 8.30 | 7.50 |
| Dimethicone 60,000 cst | 3.00 | 3.00 | 3.00 | 3.00 | 3.00 | 3.00 | 3.00 | 3.00 | 3.00 | 3.00 |
| Preservative, fragrance, color | q.s. | q.s. | q.s. | q.s. | q.s. | q.s. | q.s. | q.s. | q.s. | q.s. |
| Stability results | Sep'd | OK | OK | OK | OK | OK | Border line | Sep'd | OK | OK |

In Examples 1–10 separation occurred in Examples that did not have any added ACULYN® 22 or ACULYN® 33 acrylate material. It was found that a minimum of 1.25–1.50% (active) of ACULYN® 22 or ACULYN® 33 acrylates is needed to stabilize a composition having 3.00% dimethicone.

Examples 11–20

Dimethicone Stabilization

The following Examples were made by the Basic Method described above using the amounts of materials shown in Table D.

TABLE D

| Ingredient | Ex 11 | Ex 12 | Ex 13 | Ex 14 | Ex 15 | Ex 16 | Ex 17 | Ex 18 | Ex 19 | Ex 20 |
|---|---|---|---|---|---|---|---|---|---|---|
| Water | q.s. | q.s. | q.s. | q.s. | q.s. | q.s. | q.s. | q.s. | q.s. | q.s. |
| ALS (28%) | 46.50 | 46.50 | 46.50 | 46.50 | 46.50 | 46.50 | 46.50 | 46.50 | 46.50 | 46.50 |
| CDEA | 2.00 | 2.00 | 2.00 | 2.00 | 2.00 | 2.00 | 2.00 | 2.00 | 2.00 | 2.00 |
| ACULYN ® 22 (30%) | 6.66 | 5.83 | 5.00 | 4.16 | 3.00 | — | — | — | — | — |
| ACUSOL ® 830 (30%) | — | — | — | — | — | 8.30 | 7.50 | 6.66 | 5.83 | 5.00 |
| Dimethicone 60,000 cst | 3.00 | 3.00 | 3.00 | 3.00 | 3.00 | 3.00 | 3.00 | 3.00 | 3.00 | 3.00 |
| Preservative, fragrance, color | q.s. | q.s. | q.s. | q.s. | q.s. | q.s. | q.s. | q.s. | q.s. | q.s. |
| Stability results | OK | OK | OK | Border line | Sep'd | OK | OK | OK | OK | OK |

The data in Table D shows that at least 1.25%–1.50% active basis ACUSOL® 830 acrylate material was needed to stabilize compositions having 3% dimethicone. See especially Examples 16–22.

Examples 21–30

Dimethicone Stabilization

The following Examples were made by the Basic Method described above using the amounts of materials shown in Table E.

TABLE E

| Ingredient | Ex 21 | Ex 22 | Ex 23 | Ex 24 | Ex 25 | Ex 26 | Ex 27 | Ex 28 | Ex 29 | Ex 30 |
|---|---|---|---|---|---|---|---|---|---|---|
| Water | q.s. | q.s. | q.s. | q.s. | q.s. | q.s. | q.s. | q.s. | q.s. | q.s. |
| ALS (28%) | 46.50 | 46.50 | 46.50 | 46.50 | 46.50 | 46.50 | 46.50 | 46.50 | 46.50 | 46.50 |
| CDEA | 2.00 | 2.00 | 2.00 | 2.00 | 2.00 | 2.00 | 2.00 | 2.00 | 2.00 | 2.00 |
| ACUSOL ® 830 (30%) | 4.16 | 3.00 | — | — | — | — | — | — | — | — |

TABLE E-continued

| Ingredient | Ex 21 | Ex 22 | Ex 23 | Ex 24 | Ex 25 | Ex 26 | Ex 27 | Ex 28 | Ex 29 | Ex 30 |
|---|---|---|---|---|---|---|---|---|---|---|
| TAB-2 | — | — | 3.00 | 2.00 | 1.50 | 1.00 | — | — | — | — |
| SAB-2 | — | — | — | — | — | — | 3.00 | 2.00 | 1.50 | 1.00 |
| Dimethicone 60,000 cst | 3.00 | 3.00 | 3.00 | 3.00 | 3.00 | 3.00 | 3.00 | 3.00 | 3.00 | 3.00 |
| Preservative, fragrance, color | q.s. | q.s. | q.s. | q.s. | q.s. | q.s. | q.s. | q.s. | q.s. | q.s. |
| Stability results | border line | Sep'd | OK | OK | Border line | Sep'd | OK | OK | Border line | Sep'd |

The data in Table E shows that at least 1.25%–1.50% of the ACUSOL® 830 acrylates (active basis) is needed to stabilize compositions having 3% dimethicone. Also, a minimum of 2% TAB-2 and/or SAB-2 is needed to stabilize compositions having 3% dimethicone. See Examples 23–30.

Examples 31–40

Dimethicone Stabilization

The following Examples were made by the Basic Method described above using the amounts of materials shown in Table F.

TABLE F

| Ingredient | Ex 31 | Ex 32 | Ex 33 | Ex 34 | Ex 35 | Ex 36 | Ex 37 | Ex 38 | Ex 39 | Ex 40 |
|---|---|---|---|---|---|---|---|---|---|---|
| Water | q.s. | q.s. | q.s. | q.s. | q.s. | q.s. | q.s. | q.s. | q.s. | q.s. |
| ALS (28%) | — | — | — | — | — | — | 22.00 | 22.00 | 22.00 | 22.00 |
| SLES-2EO (28%) | 43.00 | 43.00 | 43.00 | 43.00 | 43.00 | 43.00 | 22.00 | 22.00 | 22.00 | 22.00 |
| CAP Betaine (30%) | 13.34 | 13.34 | 13.34 | 13.34 | 13.34 | 13.34 | 10.00 | 10.00 | 10.00 | 10.00 |
| CDEA | — | — | — | — | — | — | 1.00 | 1.00 | 1.00 | 1.00 |
| ACULYN® 33 (28%) | — | 5.35 | — | — | — | — | 5.35 | — | — | — |
| ACULYN® 22 (30%) | — | — | 5.00 | — | — | — | — | 5.00 | — | — |
| ACUSOL® 830 (30%) | — | — | — | — | — | — | — | — | 5.00 | — |
| Dimethicone 60,000 cst | 3.00 | 3.00 | 3.00 | 3.00 | 3.00 | 3.00 | 3.00 | 3.00 | 3.00 | 3.00 |
| Preservative, fragrance, color | q.s. | q.s. | q.s. | q.s. | q.s. | q.s. | q.s. | q.s. | q.s. | q.s. |
| DSDAC | — | — | — | — | — | 0.20 | 0.20 | 0.20 | 0.20 | 0.20 |
| TAB-2 | — | — | — | 2.50 | — | — | — | — | — | 2.50 |
| SAB-2 | — | — | — | — | 2.50 | 2.50 | — | — | — | — |
| Stability results | Sep'd | OK | OK | OK | OK | OK | OK | OK | OK | OK |

The data in Table F shows the stabilization of 3% dimethicone in different anionic as well as amphoteric systems.

Examples 41–50

Dimethicone Stabilization

The following Examples were made by the Basic Method described above using the amounts of materials shown in Table G.

TABLE G

| Ingredient | Ex 41 | Ex 42 | Ex 43 | Ex 44 | Ex 45 | Ex 46 | Ex 47 | Ex 48 | Ex 49 | Ex 50 |
|---|---|---|---|---|---|---|---|---|---|---|
| Water | q.s. | q.s. | q.s. | q.s. | q.s. | q.s. | q.s. | q.s. | q.s. | q.s. |
| ALS (28%) | 22.00 | 22.00 | — | 43.00 | — | — | — | — | — | — |
| SLES-2EO (28%) | 22.00 | 22.00 | 43.00 | — | 43.00 | 43.00 | 43.00 | 43.00 | 43.00 | 43.00 |
| CAP Betaine (30%) | 10.00 | 10.00 | 13.34 | 16.67 | 13.34 | 13.34 | 13.34 | 13.34 | 13.34 | 13.34 |
| CDEA | 1.00 | 1.00 | — | — | — | — | — | — | — | — |
| ACULYN® 33 (28%) | — | — | 5.35 | 7.14 | — | — | — | — | — | 5.90 |
| ACULYN® 22 (30%) | — | — | — | — | 5.00 | — | — | — | — | — |
| ACUSOL® 830 (30%) | — | — | — | — | — | 5.00 | — | — | — | — |
| Dimethicone 60,000 cst | 3.00 | — | 3.00 | — | 3.00 | 3.00 | — | — | — | — |
| Preservative, fragrance, color | q.s. | q.s. | q.s. | q.s. | q.s. | q.s. | q.s. | q.s. | q.s. | q.s. |
| DSDAC | 0.20 | 0.20 | — | — | — | — | — | — | — | — |
| TAB-2 | — | 2.50 | — | 2.50 | — | — | — | 2.50 | — | — |
| SAB-2 | 2.50 | — | — | — | — | — | — | — | 2.50 | — |
| Zinc Pyrithione ("ZPT", 50%) | — | 2.00 | 2.00 | 2.00 | 2.00 | 2.00 | 2.00 | 2.00 | 2.00 | 2.00 |
| Stability results | OK | OK | OK | OK | OK | OK | Sep'd | OK | OK | OK |

The data in Table G shows the stabilization of 3% dimethicone in different anionic as well as amphoteric systems and their mixtures. Also, these Examples reflect the stabilization of compositions having ZPT.

Examples 51–60

Dimethicone Stabilization

The following Examples were made by the Basic Method described above using the amounts of materials shown in Table H.

All stabilizers shown in Table H stabilize ZPT in shampoos with or without dimethicone. It is also noted that cationic polymers such as CDEA and DSDAC do not interfere with stability.

Examples 61–63

Dimethicone Stabilization With ZPT

The following Examples were made by the Basic Method described above using the amounts of materials shown in Table I.

TABLE H

| Ingredient | Ex 51 | Ex 52 | Ex 53 | Ex 54 | Ex 55 | Ex 56 | Ex 57 | Ex 58 | Ex 59 | Ex 60 |
|---|---|---|---|---|---|---|---|---|---|---|
| Water | q.s. | q.s. | q.s. | q.s. | q.s. | q.s. | q.s. | q.s. | q.s. | q.s. |
| SLES-2EO (28%) | 43.00 | 43.00 | 43.00 | 43.00 | 43.00 | 43.00 | 43.00 | 43.00 | 43.00 | 43.00 |
| Polyquaternium-10 (100%) | — | — | — | 0.20 | — | 0.20 | — | 0.20 | — | — |
| Polyquaternium-7 (8%) | — | — | — | — | 2.50 | 2.50 | — | 2.50 | — | — |
| CAP Betaine (30%) | 13.34 | 13.34 | 13.34 | 13.34 | 13.34 | 13.34 | 13.34 | 13.34 | 13.34 | 13.34 |
| CDEA | — | — | 0.50 | 0.50 | 0.50 | 0.50 | 0.50 | 0.50 | 0.50 | 0.50 |
| ACULYN® 33 (28%) | — | — | 5.90 | 5.90 | 5.90 | 5.90 | 5.90 | 5.90 | 5.90 | 5.90 |
| ACULYN® 22 (30%) | 5.50 | — | — | — | — | — | — | — | — | — |
| ACUSOL® 830 (30%) | — | 5.50 | — | — | — | — | — | — | — | — |
| Dimethicone 60,000 cst | — | — | 3.00 | 3.00 | 3.00 | 3.00 | 3.00 | 3.00 | 4.00 | 5.00 |
| Preservative, fragrance, color | q.s. | q.s. | q.s. | q.s. | q.s. | q.s. | q.s. | q.s. | q.s. | q.s. |
| Cationic guar gum | — | — | — | — | — | — | — | 0.25 | 0.25 | — |
| DSDAC | — | — | 0.20 | 0.20 | 0.20 | 0.20 | 0.20 | 0.20 | — | — |
| ZPT (50%) | 2.00 | 2.00 | 2.00 | — | — | — | — | — | — | — |
| Stability results | OK | OK | OK | OK | OK | OK | OK | OK | OK | OK |

| Ingredient | Ex. 61 | Ex. 62 | Ex. 63 |
|---|---|---|---|
| water | q.s. | q.s. | q.s. |
| ALS (28%) | — | 43.00 | 43.00 |
| SLES-2EO (28%) | 43.00 | — | — |
| CAP Betaine (30%) | 13.34 | 13.34 | — |
| CDEA (90%) | — | — | 2.00 |
| ACULYN ® 33 | 5.90 | 7.14 | 7.14 |
| Dimethicone (60,000 cst) | 3.00 | — | — |
| Misc. (preservative, color, perfume) | q.s. | q.s. | q.s. |
| ZPT (50%) or Climbazole | — | 2.00 | 2.00 |
| Stability | OK | OK | OK |

Examples 62 and 63 show that ZPT and silicone oils are stabilized in the system when different anionics are used. This is important since it shows that ZPT (which is a powder) is stabilized in the system of the invention.

Examples 64–70

The following Examples in Table J are shampoo formulations made in accordance with this invention. The general method for making these formulations is the Basic Method as described above with the amounts of ingredients shown in Table J.

TABLE J

| Ingredient | Ex. 64 | Ex. 65 | Ex. 66 | Ex. 67 | Ex. 68 | Ex. 69 | Ex. 70 |
|---|---|---|---|---|---|---|---|
| water | q.s. | q.s. | q.s. | q.s. | q.s. | q.s. | q.s. |
| ALS (28%) | 45.00 | 45.00 | 45.00 | 45.00 | — | — | — |
| SLES-2EO (28%) | — | — | — | — | 43.00 | 43.00 | 43.00 |
| Polyquaternium-10 | 0.05 | 0.10 | 0.10 | 0.15 | 0.05 | 0.10 | 0.10 |
| CAP Betaine (30%) | — | — | — | — | 13.34 | 13.34 | 13.00 |
| CDEA (90%) | 1.85 | 1.85 | 1.85 | 1.85 | 0.60 | 0.60 | 0.60 |
| ACULYN 33 | 5.00 | 5.35 | 5.89 | 5.89 | 5.00 | 5.35 | 5.89 |
| Dimethicone 60,000 cst | 1.50 | 2.50 | 3.00 | 3.50 | 1.50 | 2.50 | 3.00 |
| Cationic guar gum | 0.10 | 0.15 | 0.20 | 0.25 | 0.10 | 0.15 | 0.20 |
| DSDAC | 0.20 | 0.20 | 0.25 | 0.25 | 0.20 | 0.20 | 0.25 |
| Misc. (preservative, color, perfume) | q.s. | q.s. | q.s. | q.s. | q.s. | q.s. | q.s. |
| Pearlizer (Tego Pearl N-100) | 2.00 | 2.00 | 2.00 | 2.00 | 2.00 | 2.00 | 2.00 |
| Stability | OK | OK | OK | OK | OK | OK | OK |

Examples 71–76

The following Examples in Table K are shampoo formulations made in accordance with this invention. The general method for making these formulations is the Basic Method as described above with the amounts of ingredients shown in Table K.

TABLE K

| Ingredient | Ex. 71 | Ex. 72 | Ex. 73 | Ex. 74 | Ex. 75 | Ex. 76 |
|---|---|---|---|---|---|---|
| Water | q.s. | q.s. | q.s. | q.s. | q.s. | q.s. |
| SLES-2EO (28%) | 43.00 | 33.00 | 33.00 | 43.00 | 43.00 | 43.00 |
| Polyquaternium-10 (100%0) | 0.15 | 0.15 | 0.35 | — | — | — |
| Polyquaternium-7 (30%) | — | 1.50 | 3.00 | 1.50 | 2.50 | 3.50 |
| CAP Betaine (30%) | 13.00 | 17.00 | 17.00 | 13.00 | 13.00 | 13.00 |
| CDEA (90%) | 0.60 | 0.60 | 0.60 | 0.60 | 0.60 | 0.60 |
| ACULYN ® 33 | 5.89 | 5.00 | 5.89 | 5.89 | 5.89 | 5.89 |
| Dimethicone 60,000 cst | 3.50 | 1.50 | 3.50 | 3.00 | 3.00 | — |
| Cationic guar gum | 0.25 | — | — | — | — | — |
| DSDAC | 0.25 | 0.25 | 0.25 | 0.25 | 0.25 | 0.25 |
| Misc. (preservative, perfume, color) | q.s. | q.s. | q.s. | q.s. | q.s. | q.s. |
| Stability | OK | OK | OK | OK | OK | OK |

*zinc pyrithione; or 1-(4-chlorophenoxy)-1-(1H-imidazolyl)-3,3-dimethyl-2-butanone)

Examples 74–76 show that ZPT and silicone oils are stabilized in the system.

Examples 101–104

The Basic Method described above was used with the following amounts of ingredients listed by Step number in Table L.

TABLE L

| Ingredient | Ex 101 | Ex 102 | Ex 103 | Ex 104 |
|---|---|---|---|---|
| Part 1 | | | | |
| filtered irradiated deionized water | q.s | q.s | q.s | q.s |
| ALS (28%) (Standapol A) | 49.00000 | 49.00000 | 46.25000 | 46.25000 |
| Part 2 | | | | |
| filtered irradiated deionized water | 2.00000 | 2.00000 | 2.00000 | 2.00000 |
| Polyquaternium-10 (Polymer JR-30M) | 0.05000 | 0.05000 | 0.10000 | 0.15000 |
| Part 3 | | | | |
| sodium phosphate dibasic | ±0.80000 | ±0.80000 | ±0.80000 | ±0.80000 |
| SCS pellets (87%) | ±0.33334 | ±0.33334 | ±1.20000 | ±1.20000 |
| Part 4 | | | | |
| fragrance | 0.50000 | 0.50000 | 0.50000 | 0.50000 |
| cationic guar gum (Cosmedia guar C-261) | 0.15000 | 0.15000 | 0.15000 | 0.15000 |
| Part 5 | | | | |
| fragrance | 0.50000 | 0.50000 | 0.50000 | 0.50000 |
| CDEA (90%) (Standamid KD) | 1.75000 | 1.75000 | 1.75000 | 1.75000 |
| DSDAC (Aerosurf TA-100) | 0.22000 | 0.22000 | 0.22000 | 0.22000 |
| Part 6 | | | | |
| acrylates copolymer (28%) (ACULYN ® 33) | 5.36000 | 5.36000 | 5.89000 | 5.89000 |
| Dimethicone (60,000 cst) | 1.75000 | 2.50000 | 2.75000 | 3.50000 |
| Part 7 | | | | |
| filtered irradiated deionized water | 2.00000 | 2.00000 | 2.00000 | 2.00000 |
| glycol distearate (and) Steareth-4 (TegoPearl N-100) | 2.00000 | 2.00000 | 2.00000 | 2.00000 |
| FD&C Blue #1 (1.00% solution) | 0.02100 | 0.02100 | 0.02100 | 0.02100 |
| FD&C Green #8 (1.00% solution) | 0.16800 | 0.16800 | 0.16800 | 0.16800 |
| Part 8 | | | | |
| preservative* (Kathon CG) | 0.07000 | 0.07000 | 0.07000 | 0.07000 |
| TOTAL | 100.00000 | 100.00000 | 100.00000 | 100.00000 |

*methylchloroisothiazolinone and methylisothiazolinone

For Examples 101–104, the viscosity is in the range of 4000–6000 cps, the pH is in the range of 6.00–6.50.

We claim:

1. A method for stabilizing a water insoluble organosilicone compound in a hair care product selected from the group consisting of conditioners and conditioning shampoos, wherein said method comprises combining the following ingredients at ambient temperature:

A. 4.00–50.00 percent of a detersive surfactant selected from the group consisting of an anionic detergent selected from the group consisting of $C_8$–$C_{18}$ alkyl sulfates, $C_8$–$C_{18}$ alkyl ethenoxy ether sulfates containing 1–5 ethenoxy groups in the molecule, $C_{10}$–$C_{18}$ acyl isethionates, $C_{10}$–$C_{20}$ alkyl sulfonates, $C_{10}$–$C_{20}$ alkylene sulfonates, and mixtures thereof; and optionally at least one of:

(1) 0.10–5.00 percent of an anionic hydrotropic, $C_1$–$C_3$ alkyl benzene sulfonate or $C_5$–$C_6$ alkyl sulfate;
(2) 0.10–15.00 percent of an amphoteric surfactant selected from the group consisting of $C_8$–$C_{18}$ alkyl betaines, $C_8$–$C_{18}$ alkyl sulfobetaines, $C_8$–$C_{18}$ alkylamido $C_2$–$C_3$ alkyl betaines, $C_8$–$C_{18}$ alkylamido $C_2$–$C_3$ alkyl sulfobetaines, $C_8$–$C_{18}$ alkyl amphoacetates, $C_8$–$C_{18}$ alkyl amphopropionates, and mixtures thereof; and
(3) 0.1–4.0 percent of a nonionic surfactant selected from the group consisting of $C_8$–$C_{22}$ monoethanolamides and mixtures there of and $C_8$–$C_{22}$ diethanolamides and mixtures thereof;

provided that the total amount of detersive surfactant does not exceed 50 percent by weight of the total weight of the composition;

B. 0.01–10.00 percent of a water-insoluble conditioning agent which is selected from the group consisting of:
(1) 0.10–6.00 percent of a water-insoluble silicone selected from the group consisting of dimethicones and silicones; and
(2) a mixture of at least one of B(1) with 0.01–3.00 percent of at least one cationic polymer;

C. 1.25–5.00 percent of an acrylic stabilizing agent selected from the group consisting of an acrylates copolymer comprising two or more monomers selected from the group consisting of acrylic acid derivatives selected from Formula III and Formula IV:

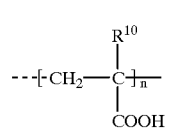

Formula III where $R^{10}$ is a member of the group consisting of hydrogen and $C_1$–$C_{22}$ alkyl group;
and n is an average value and is a number from 3–4100, and is selected so that the molecular weight is in the range of 218–1,000,000; and

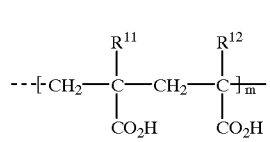

Formula IV where $R^{11}$ and $R^{12}$ are each independently selected from the same group defined for $R^{10}$, and m is selected from the same group as defined for n, and wherein a neutralization step is performed with a member selected from the group consisting of cosmetically acceptable bases and, optionally, the acrylates has been partially esterified with a member of the group consisting of $C_3$–$C_{22}$ aliphatic alcohols; and D. the balance as water or an aqueous medium.

2. The method as claimed in claim 1 wherein the cationic polymer is a polyquaternary compound selected from the group consisting of (a) quaternized cellulosic polymers and (b) a mixture of at least one quaternized cellulosic polymer with a non-cellulosic quaternary conditioning polymer.

3. The method as claimed in claim 1 wherein the water insoluble organosilicone compound is selected from the group consisting of:
(a) dimethicones and dimethicone derivatives of Formula I and mixtures thereof:

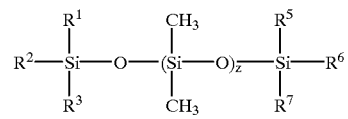

Formula I wherein $R^1$, $R^2$, $R^3$, $R^5$, $R^6$, and $R^7$ are each independently selected from the group consisting of alkyls of 1–6 carbons, and z is selected so that the dimethicones and dimethicone derivatives have a viscosity in the range of 5–100,000 centipoise and mixtures thereof; and
(b) aminosilicones of Formula II

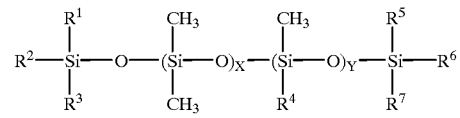

Formula II wherein $R^1$, $R^2$, $R^3$, $R^5$, $R^6$, and $R^7$ are each independently selected from the group consisting of alkyls of 1≠6 carbons; and $R^4$ is $R^8$—NH—$CH_2CH_2$—$NH_2$, where $R^8$ is an alkylene of 3–6 carbons;
x= is an average value and is a number in the range of 500–10,000; and
y= is an average value and is a number in the range of 1–10.

4. A method as claimed in claim 3 where the dimethicones, dimethicone derivatives and mixtures thereof have a viscosity in the range of 30–70,000 centipoise.

5. A method as claimed in claim 3 where the aminosilicones of Formula II are selected so that x= a number in the range of 500–4,000, and y is less than 5.

6. A method as claimed in claim 5 where the aminosilicones of Formula II are selected so that x= a number in the range of 500–1000.

7. A method as claimed in claim 1 wherein the cosmetically acceptable bases are selected from the group consisting of sodium hydroxide; sodium phosphate, dibasic; and $C_3$–$C_{22}$ aliphatic amines.

8. A method as claimed in claim 1 wherein the stabilizing agent is used as a complex formed with a member selected from the group consisting of cationic monomers.

9. A method as claimed in claim 8 wherein the cationic species to form the complex with the stabilizing agent is selected from the group consisting of cetyl trimethyl ammonium chloride, distearyl diammonium chloride, Polyquaternium-6, Polyquaternium-7, Polyquaternium-10, cationic guar gum, and cosmetically acceptable polycationics.

10. A method as claimed in claim 1 wherein the detersive surfactant is 1.00–35.0 percent by weight based on the total weight of the composition of an anionic detergent selected from the group consisting of water soluble $C_8$–$C_{22}$ lipophilic sulfates and $C_8$–$C_{22}$ lipophilic sulfonates.

11. A method as claimed in claim 1 wherein the detersive surfactant is 6.00–30.00 percent by weight of the total composition.

12. A method as claimed in claim 10 wherein the water soluble lipophilic sulfates and lipophilic sulfonates each have 8–22 carbon atoms.

13. A method as claimed in claim 10, wherein the anionic detergent is selected from the group consisting of $C_{10}$–$C_{18}$ alkyl sulfates, $C_{10}$–$C_{18}$ paraffin sulfonates, $C_{10}$–$C_{18}$ olefin sulfonates, $C_{10}$–$C_{18}$ fatty acid monoglyceride sulfates, $C_{10}$–$C_{18}$ fatty alcohol $C_1$–$C_6$ lower alkoxy sulfates, linear $C_8$–$C_{18}$ alkyl benzene sulfonates, and $C_8$–$C_{18}$ is dialkyl sulfosuccinates.

14. A method as claimed in claim 10, wherein the anionic detergent is selected from the group consisting of $C_8$–$C_{16}$ alkyl sulfates, and $C_8$–$C_{18}$ alkyl $C_1$–$C_6$ alkoxy sulfates.

15. A method as claimed in claim 10 wherein the anionic detergent is selected from the group consisting of $C_{12}$ alkyl $C_{2-3}$ alkoxy sulfate, $C_{12}$ alkyl ethoxy sulfate and $C_{10}$–$C_{18}$ fatty alcohol ethoxy sulfates.

16. A method as claimed in claim 14 wherein the anionic detergent is a mixture of $C_{10}$–$C_{18}$ alkyl sulfate and $C_{10}$–$C_{18}$ alkyl ether sulfate, with either sulfate being present in greater or equal proportion, and with the ratio of amounts of such components being in the range of 10:1 to 1:10.

17. A method as claimed in claim 10 wherein the detersive surfactant comprises 0.05–10.00 percent by weight based on the total weight of the composition of an anionic hydrotrope.

18. A method as claimed in claim 10 wherein the detersive surfactant comprises 0.50–15.00 percent by weight based on the total weight of the composition of an amphoteric surfactant selected from the group consisting of cocoamidopropylbetaines, sodium laureth-2-sulfosuccinate, amphopropionic acid, cocamidobetaine, cocobetaine, cocobetainamido sodium lauriminodipropionate, dodecyl dimethylamine oxide, octyl dimethylamine oxide, octadecyl dimethylamine oxide, cocamidopropylamine, cocoamphodipropionic acid, and cocamidopropylhydroxy sultaine.

19. A method as claimed in claim 1 wherein the cationic polymers are derivatives of natural polymers selected from the group consisting of cellulose and gums which are water-soluble to the extent of at least 0.5 percent by weight at 20 degrees C., have more than 10 monomer units in their molecules and a molecular weight in the range of 1000–1,00,000, and wherein the cationic portion is cosmetically acceptable.

20. A method as claimed in claim 19 wherein the molecular weight of the cationic polymer is in the range of 2000–500,000.

21. A method as claimed in claim 19 wherein the cationic portion is a quaternary group.

22. A method as claimed in claim 21 wherein the quaternary group is an alkyl ammonium group selected from the group consisting of $C_8$–$C_{22}$ amidopropyl dimethylamine, $C_8$–$C_{22}$ amidopropyl morpholine; $C_8$–$C_{22}$ amine oxide; and mixtures thereof.

23. A method as claimed in claim 19 wherein the cationic polymer is formed with hydroxy alkyl celluloses and alkyl hydroxy alkyl celluloses.

24. A method as claimed in claim 19 wherein the cationic polymer is formed from hydroxy ethyl celluloses having a molecular weight of 150,000–400,000 and a degree of substitution off a quaternary group of about 0.3.

25. A method as claimed in claim 19 wherein the cationic polymer is formed from alkyl hydroxy celluloses which have additional alkyl substituents at other sites on an anhydroglucose unit, have a molecular weight in the range of about 50,000–500,000 and a degree of substitution of about 0.1–0.8.

26. A method as claimed in claim 19 wherein the cationic polymer is a galactomannan gum.

27. A method as claimed in claim 26 wherein the galactomannan is selected from the group consisting of guar gum and hydroxy alkylated guar gum having a molecular weight of 100,000–1,000,000.

28. A method as claimed in claim 19 wherein the cationic polymer is a polymeric quaternary ammonium salt of hydroxyethyl cellulose reacted with a trimethyl ammonium substituted epoxide.

29. A method as claimed in claim 1 comprising the following steps:
 a) forming a main mixture by combining water and a surfactant;
 b) separately preparing a dispersion of a cationic polymer in water;
 c) adding the dispersion of cationic compound in water to the main mixture of water and surfactant to form a gel with continued mixing as needed until a smooth, homogeneous gel is formed;
 d) adjusting the pH of the main mixture to 5.0–8.0;
 e) adding a surfactant to the gel and mixing until the main mixture is uniform;
 f) separately adding a thickening agent and optionally a portion of fragrance;
 g) mixing the main mixture until uniform;
 h) adding a foam booster and fragrance which have been optionally separately prepared with a thickening agent;
 i) mixing the main mixture until uniform;
 j) adding an acrylates copolymer as a stabilizing agent to the main mixture;
 k) mixing the main mixture until uniform;
 l) adding optional ingredients with mixing;
 m) cooling the main mixture if needed;
 n) adjusting pH of the main mixture to 4–8;
 o) adjusting viscosity of the main mixture to 1500–10,000 cps; and
 p) filtering product.

30. A method as claimed in claim 29 wherein the cationic polymer is a polyquaternary compound.

31. A shampoo made by the method of claim 1.

32. A method as claimed in claim 1 wherein the acrylates copolymer is ACULYN 33.

* * * * *